(12) United States Patent
Yu

(10) Patent No.: US 12,426,805 B2
(45) Date of Patent: Sep. 30, 2025

(54) REMOTE SENSOR BASED METHOD AND SYSTEM FOR MONITORING A SUBJECT

(71) Applicant: Yiu Tong Yu, Hong Kong (CN)

(72) Inventor: Yiu Tong Yu, Hong Kong (CN)

( * ) Notice: Subject to any disclaimer, the term of this patent is extended or adjusted under 35 U.S.C. 154(b) by 503 days.

(21) Appl. No.: 18/072,733

(22) Filed: Dec. 1, 2022

(65) Prior Publication Data
US 2023/0172489 A1 Jun. 8, 2023

Related U.S. Application Data

(60) Provisional application No. 63/286,742, filed on Dec. 7, 2021.

(51) Int. Cl.
*A61B 5/11* (2006.01)
*A61B 5/00* (2006.01)

(52) U.S. Cl.
CPC .......... *A61B 5/1113* (2013.01); *A61B 5/0064* (2013.01); *A61B 5/74* (2013.01)

(58) Field of Classification Search
CPC .... A61B 5/1113; A61B 5/1115; A61B 5/1117; A61B 5/0064; A61B 5/74; A61B 5/1128; A61B 2503/08; G08B 21/0423; G08B 21/0469; G01S 13/89; G01S 17/894; G06V 20/64
See application file for complete search history.

(56) References Cited

U.S. PATENT DOCUMENTS 7,106,885 B2 * 9/2006 Osterweil ................. G06T 7/50
348/E13.005

OTHER PUBLICATIONS

Cheung et al., Night-Time Monitoring System (eNightLog) for Elderly Wandering Behavior, Sensors, Jan. 2021, 21, 704, www.mdpi.com/journal/sensors, Basel, Switzerland.

* cited by examiner

*Primary Examiner* — Kent Yip
(74) *Attorney, Agent, or Firm* — NCC-IP; Nevin Stuart Carmichael

(57) ABSTRACT

The invention provides a method and a system of monitoring a subject. The method comprises the steps of monitoring, from a first angle of detection, a space in which the subject is located to obtain data of the subject from a first perspective view in accordance with the first angle of detection; converting the obtained data of the subject into a three-dimensional data set; processing the three-dimensional data set to create an image of the subject from a second perspective view, said second perspective view being created at a second angle different from the first angle of detection; and analyzing the created image from the second perspective view to determine, calculate, or select one or more characteristics relating to activity of the subject being monitored.

18 Claims, 3 Drawing Sheets

REMOTE SENSOR BASED METHOD AND SYSTEM FOR MONITORING A SUBJECT

FIELD OF THE INVENTION

The invention relates to the field of monitoring a subject. Particularly but not exclusively, the invention relates to a system and a method for monitoring one or more subjects for the purpose of identifying potential risks.

BACKGROUND OF THE INVENTION

Various monitoring systems have been developed for use in detecting and monitoring motion and/or activity of subjects and particularly, for monitoring patients, disables and/or elderlies in healthcare settings such as hospitals, nursing homes, elderly centers or for home-care applications with an aim to improve safety of the patients or residents. Conventional monitoring systems are mostly equipped with cameras or video-cameras arranged within a predetermined distance and/or direction from the subject in a space to capture images or videos of the subject. Optionally, conventional systems are often required for the subject to be provided with pressure mat, sensor pad and/or wearable sensor to increase sensitivity on detecting movement of the subject such as to detect an off-bed movement. Other monitoring systems may include sensors based on invisible barriers such as infra-red fences which operate by transmitting and receiving infra-red beams, and that an alarm can be triggered when a 'break' to the infra-red beams is detected. Journal article "*Night-Time Monitoring System 9eNightLog) for Elder Wandering Behavior*, Sensors 2021, 21, 704, Cheung, J. C.-W., et. al." discloses a remote sensor-based system for monitoring wandering behavior of elder. However, the sensor of Cheung requires installation of the sensor at the ceiling and above the bed of the subject being monitored. This restriction is highly not preferable especially for the sensor be applied in shared locations such as hospitals, as bed settings are often changeable depending on usage and occupancy of the room.

The existing technologies are therefore known to suffer from lack of sensitivity and thus accuracy on their detections. Applications are also limited by their installation positions and ranges of detection of the sensors. The results are that false alerts are often generated which are undesirable. The use of cameras or video-cameras for monitoring subjects may further raise privacy concerns, and therefore, are generally not allowable for use in places such as toilets and bathrooms where falls and other accidents are likely to happen.

OBJECTS OF THE INVENTION

An object of the present invention is to provide a method and a system for monitoring a subject.

Another object of the present invention is to mitigate or obviate to some degree one or more problems associated with known monitoring systems, or at least to provide a useful alternative.

The above objects are met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect, the invention provides a method of monitoring a subject. The method comprises the steps of monitoring, from a first angle of detection, a space in which the subject is located to obtain data of the subject from a first perspective view in accordance with the first angle of detection; converting the obtained data of the subject into a three-dimensional data set; processing the three-dimensional data set to create an image of the subject from a second perspective view, said second perspective view being created at a second angle different from the first angle of detection; analyzing the created image from the second perspective view to determine, calculate, or select one or more characteristics relating to activity of the subject being monitored.

In a second main aspect, the invention provides a system for use in monitoring a subject. The system comprises a sensor adapted to monitor, from a first angle of detection, a space in which the subject is located to obtain data of the subject from a first perspective view in accordance with the first angle of detection; a processing module adapted to convert the obtained data of the subject into a three-dimensional data set, and process the three-dimensional data set to create an image of the subject from a second perspective view, said second perspective view being created at a second angle different from the first angle of detection; and an analyzing module adapted to analyze the created image from the second perspective view to determine, calculate, or select one or more characteristics relating to activity of the subject being monitored.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figure, of which.

DESCRIPTION OF PREFERRED EMBODIMENTS

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

The present invention relates to a method and a system for monitoring a subject, such as a human subject or an animal subject. Particularly but not exclusively, the present invention relates to a remote sensor-based system for real-time detecting and monitoring one or more subjects which can be, for example, patients, disables and/or elderlies in locations such as, but are not limited to, hospitals, nursing homes, elderly centers and/or residential areas, etc. A plurality of subjects located in the same location can be simultaneously detected and monitored by a single sensor unit. Alternatively, multiple sensors may also be applied for a synchronized detection to improve sensitivity and accuracy of the detection. The use of remote sensor negates the need of any cameras, video-cameras or the like for capturing images or videos of the space, which are known to create privacy concerns to the subjects being monitored.

Figure 1:
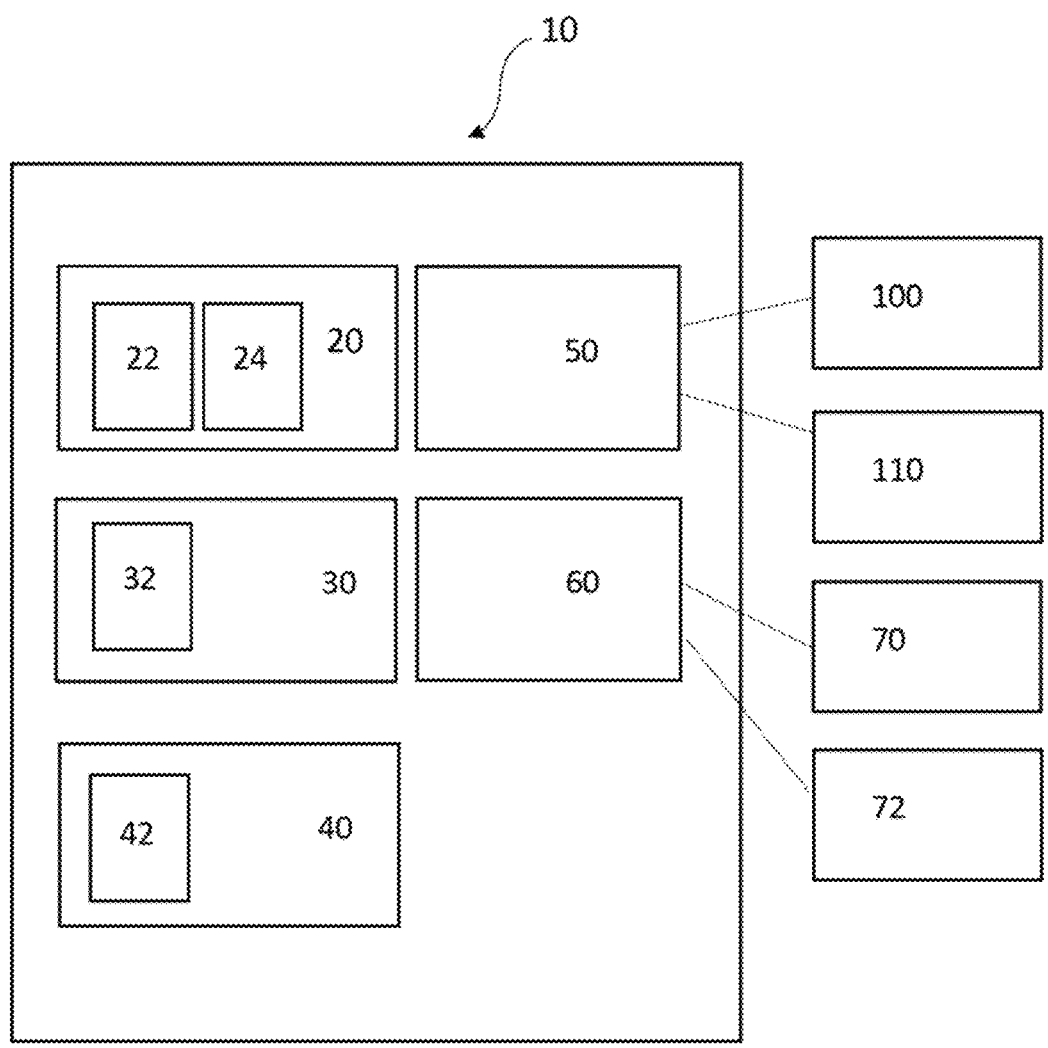
FIG. 1 is a block schematic diagram showing a system for monitoring a subject according to the present invention.
Figure 2:
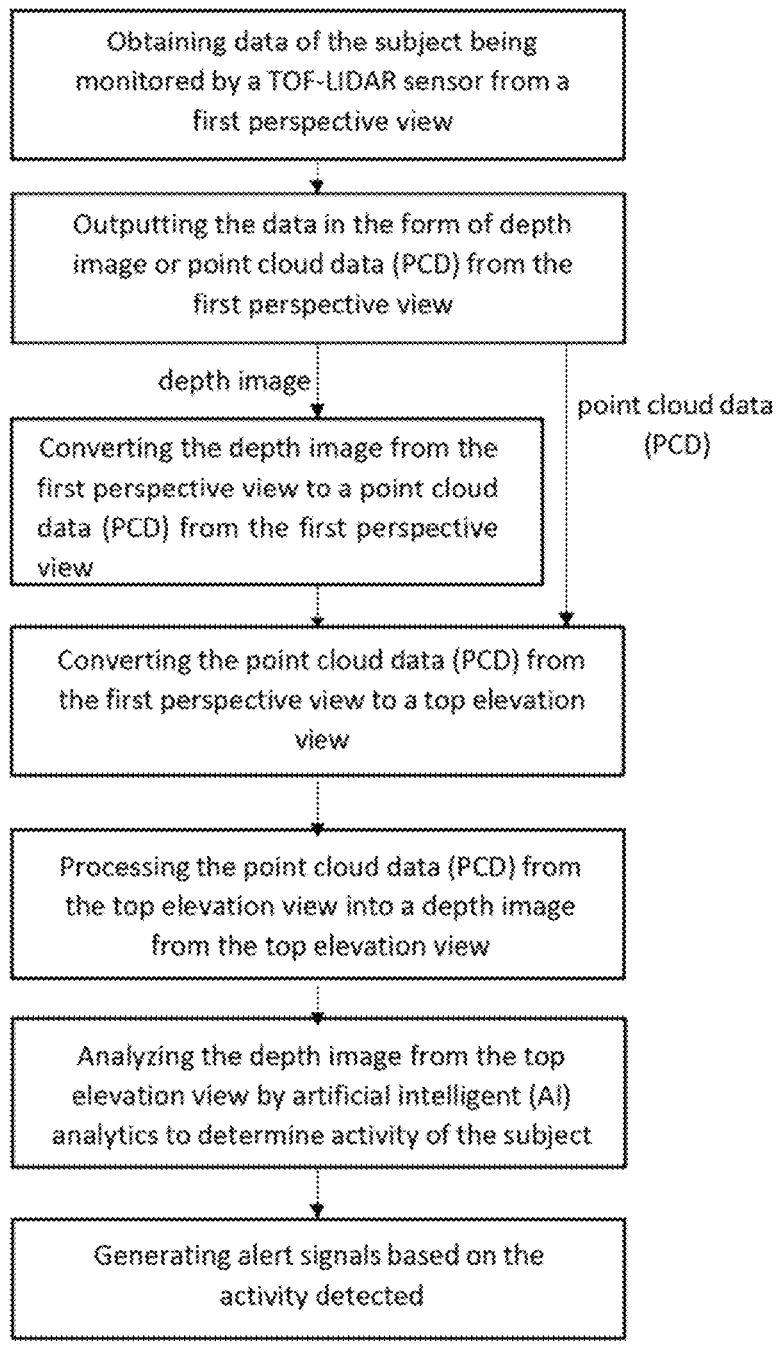
FIG. 2 is a flow diagram showing a method of monitoring a subject implemented at the system of FIG. 1.

Referring to FIGS. 1 and 2, shown is a system 10 and a method for monitoring a subject or a plurality of subjects in a space in accordance with an embodiment of the present invention. The system 10 comprises a sensor 20 for remote monitoring, from a first angle of detection, a space such as a room of a nursing home, an elderly facility or a hospital ward, in which the one or more subjects are located. Particularly, the sensor 20 is adapted to obtain data of the subject being monitored from a first perspective view in accordance with the first angle of detection. The sensor 20 can be mounted, placed or generally arranged at any locations or positions in the space or the room. For example, the sensor 20 can be mounted at a level horizontal to the subject such as at a side wall of the room, or at a side, elevated position such as at a corner of the room, etc. The sensor 20 is therefore not limited to be provided at any specific locations of the room, such as, as required by the prior technology, at the ceiling and above the subject being monitored to avoid interference or occlusion to the line of detection. Preferably, the sensor 20 provides a range of detection of about 0.1 meter to about 20 meters. Operation of the sensor 20 is not affected by the lighting conditions of the space under detection, and that the sensor 20 is capable of monitoring subjects at high sensitivity and accuracy even in a dark environment such as at night time, or under high ambient light.

In one embodiment, the sensor 20 may comprise an emitter 22 for emitting light pulses such as electromagnetic radiation at the first angle of detection towards the subject, and a receiver 24 for receiving the electromagnetic radiation reflected from the subject to thereby determine distance information of the subject relative to the sensor 20. The sensor 20 will then process the distance information of the subject into the data of the subject from the first perspective view in accordance with the first angle of detection. The electromagnetic radiation preferably comprises infra-red (IR) radiation, but other radiation or a combination of radiations may also be applicable as long as it is reasonably suitable for the purpose of the invention. In one embodiment, the sensor 20 may comprise a time of flight (TOF) sensor. In another embodiment, the sensor 20 may comprise a light detection and ranging (LIDAR) sensor, which can be but is not limited to a rotating LIDAR sensor or a solid-state LIDAR sensor. Preferably, the sensor 20 comprises a combined time of flight, light detection and ranging (TOF-LIDAR) sensor as a single unit thereby allowing a reduced size of the sensor 20 and the system 10.

In one embodiment, the distance information of the subject relative to the sensor 20 can be calculated by time of flight measurement based on the following equation:

$$t = \text{time}, d = \text{distance}, d = \frac{c*t}{2}$$

wherein t represents the time taken for the emitted radiation to be detected by the receiver 24 after being reflected from the subject; c represents the speed of light; and d represents the distance between the sensor 20 and the subject.

After the time of flight measurement, the sensor 20 may output the obtained data in the form of a depth image and/or a point cloud data set. The data can be transferred from the sensor 20 via any known wired connection, USB ports, or being transferred wirelessly via a network interface of the system 10. The data may further be communicated to a remote network 100 or a cloud-based database 110 via a communication module 50 of the system 10. It is important to note that all of the data acquired, transferred, processed and stored are in the form of digital signals, and that no images or videos are kept or stored in the system 10 to protect privacy of the subjects being monitored.

The system 10 may further comprise a processing module 30 adapted to receive and convert the obtained data of the subject into a three-dimensional data set. In one embodiment, the three-dimensional data set may comprise a three-dimensional point cloud data (PCD), and that the converting step comprises processing the data of the subject from the first perspective view into a point cloud data from the first perspective view. In the present invention, the term "point cloud data (PCD)" is given a general meaning to refer to a set of data points in space, with each data point representing a specific point position with X, Y and Z coordinates of the subject being monitored. The point cloud data from the first perspective view from the sensor 20 can be stored at a memory 32 of the processing module 30.

In another embodiment, the data of the subject may comprise a depth image or a depth map from the first perspective view. The depth image will subsequently be converted into the point cloud data (PCD) from the first perspective view. The conversion from depth image to point cloud data (PCD) can be conducted based on the following equations:

$$z = d$$
$$x = (i - w/2)*z$$
$$y = (j - h/2)*z$$

wherein d represents the depth information contained in the depth image; i represents the row number of a pixel in the depth image; j represents the column number the pixel in the depth image; w represents the width of the depth image; h represents the height of the depth image; and x, y and z represent the respective coordinates of converted point cloud data (PCD).

In the context of the present invention, the term "depth image" or "depth map" generally relates to an image having pixel values at the x and y coordinates and containing depth values represented by luminance gradients in proportion to distance with reference to the point of view. For example, a depth image may represent depth information of a subject with a nearer surface being shown brighter and a further away surface being shown darker, or vice versa.

After the conversion, the point cloud data from the first perspective view will be stored at the memory 32 of the processing module 30. Optionally, a background or reference data may priorly be obtained from the first perspective view which will be subtracted from the data of the subject from the first perspective view to remove background objects from the processing steps. In one embodiment, a marker which can be formed of a light reflective material can be used to provide marking on a reference substrate or a reference region of space on which or in which presence of the subject is most likely to thereby assist detection of the subject by the sensor 20.

The processing module 30 may further convert the point cloud data (PCD) from the first perspective view into a point cloud data (PCD) from the second perspective view, and process the point cloud data (PCD) from the second perspective view into a depth image from the second perspective view, wherein said second perspective view is created at a second angle different from the first angle of detection. In one embodiment, the processing of the point cloud data (PCD) from the second perspective view into a depth image from the second perspective view can be conducted by projecting the point cloud data onto a x-y plane to form a depth image viewed from the same perspective. The processing of the point cloud data (PCD) from the second perspective view into a depth image from the second perspective view is conducted with an aim to prepare the data into a processible format by the analyzing module 40, which steps will be discussed further below.

Figure 3:
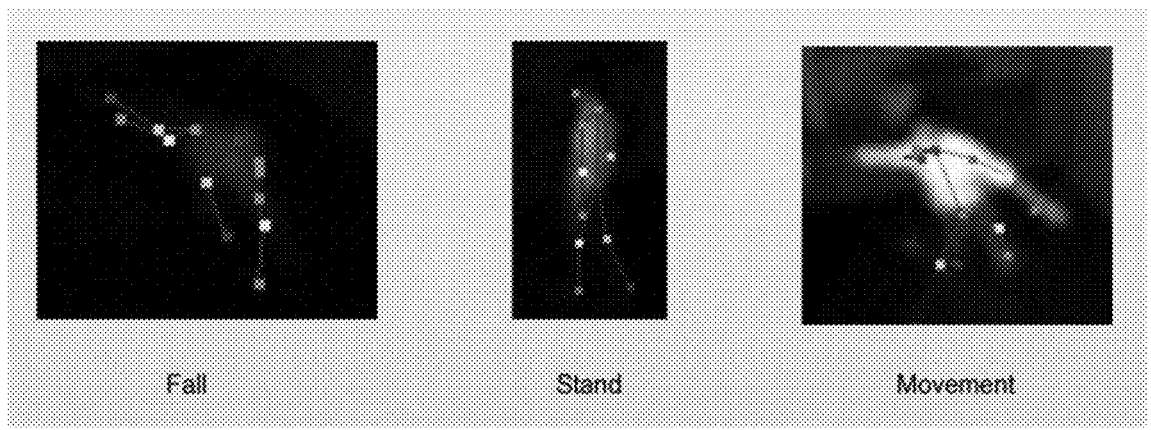
FIG. 3 are depth images showing posture or motion of subjects from a first perspective view.
Figure 4:
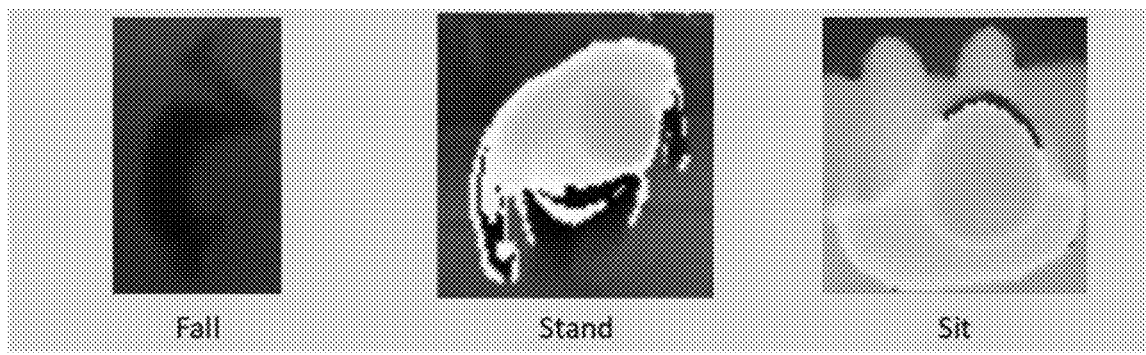
FIG. 4 are depth images showing posture or motion of subjects from a second perspective view.

In one embodiment, the second perspective view is preferably different to the first perspective view. For example, the second perspective view can be a top elevation view of the subject being monitored (see FIG. 4), while the first perspective view can be a horizontal view, a diagonal view or a view from any angle based on the direction of detection of the sensor 20 (see FIG. 3). The top elevation view may comprise a bird's eye view. In one further embodiment, the top elevation view may comprise a wide-angled view for a widened field of view.

The system 10 may further comprise an analyzing module 40 adapted to analyze the created depth image from the second perspective view to determine, calculate, or select one or more characteristics relating to activity of the subject being monitored. The characteristics relating to activity of the subject may generally comprise one or more of a posture, a motion, an orientation, a speed of motion and any general activity of the subject being monitored. The characteristics may further be determined by processing based on a computer implemented algorithm, for example, by calculating one or more depth values of the detected subject with reference to one or more preset base lines or reference objects which can be, for example, a bed surface, a floor surface, a chair or a bench top, to thereby determine motion or activity of the subject by inference such as whether the subject is lying on bed, sitting on a chair, having a meal, or have fallen to the ground. In one embodiment, the analyzing module 40 may further comprise a machine learning module 42 for a real-time analysis on the depth image based on artificial intelligent (AI) analytics. The analysis may involve machine learning algorithms which can be, but are not limited to, convolution neutral networks (CNN). The CNN is capable of automatically selecting features from the depth image from the top elevation view and recognizing postures, motions and/or activities of the subjects based on continuous training. For example, the activity of the subject as predicted based on the determined, calculated, or selected characteristics of analyzed image may comprise one or more of lying down, sitting, standing, walking, falling, exiting bed, and exiting the space being monitored. In one embodiment, the machine learning module 42 may comprise one or more of a Google coral series computing module and/or a Nvidia Jetson series computing module.

In one embodiment, continuous data can be acquired by the sensor 20 and be processed by the processing module 30 to create a series of depth images or a video clip for the machine learning analysis to allow a more in-depth analysis on the activity based on both content and context of the images and/or the videos.

In response to the different activities of the subject detected, a signaling module 60 of the system 10 may generate one or more alert signals to inform the caretakers of any potential risks. For example, a first alert signal can be produced when an activity of the subject at a relatively lower risk is detected or inferred, for example, when the posture or motion of the subject is detected to change from lying in bed to sitting on a chair. A second alert can also be produced when an activity of the subject at a relatively higher risk is detected, for example, the posture or motion of the subject is detected to change from lying in bed to lying on the floor implying a fall event, or when the subject has exited the space being monitored. The different levels of alert signals signify whether an immediate attention or assistance is required from the caretakers. In one embodiment, the higher risk, second alert signal can be produced after the lower risk, first alert signal is triggered and maintained for a predetermined period of time, i.e. with no human interference such as to manually switch off and/or to cancel the alert, implying attention has not yet been given to the subject's activity which caused the first alert event.

The generated first and/or the second alert signals can be outputted, via the signalling module 60, in the form of one or more of visible and audible alert or alarm to one or more alarm devices 72. A second alert signal, which suggests a possible higher risk of the subject, can be provided in the form of a relatively louder, longer and/or continuous beeping with an alarm lighting, such as a red revolving light, to signal that an immediate attention is required; while a first alert signal, which suggests a possible lower risk to the subject, can be provided in the form of a relatively softer, shorter, and/or intermittent beeping with a more moderate alarm lighting. The visible and/or audible alert signals may generally be provided by any known alarm devices 72 such as flashlights, speakers, alarms or the like, and the devices are preferably arranged away from the room being monitored such as at the work-stations of the caretakers to avoid alarming the patients.

The communicating module 50 may further communicating the alert signals, either wiredly or wirelessly, to one or more computer devices 70 in any known form such as desk top computers, laptop computers, tablet computers, smart phones, any portable or wearable electronic smart devices or other emergency service systems. The communication module 50 may also transmit the alert signals to a network 100, either private or public such as the internet, or a cloud-based server 110, to keep record of all the detected risk events or to exchange information or data. In one embodiment, the alert signals can be transmitted wirelessly between the system 10 and one or more of the computer devices 70, the network 100 and the cloud-based server 110. For example, in a situation in which the lower risk, first alert signal has been maintained for a predetermined period of time, e.g. after 20 seconds, and the system 10 has failed to detect any intervention or interference such as for the caretakers to switch off the alarm, a higher risk, second alert signal may be generated. Simultaneously or subsequently, a warning which can be provided in the form of a phone call or a text message may be sent wirelessly via the communicating module 50 to one or more emergency contacts preset at with the system 10. In one other embodiment, the warning message may optionally be attached with location details of the subject which can be sent to the subject's emergency contacts and/or the emergency system, for example.

The present invention is advantageous in that it provides a remote sensor-based monitoring system comprising a time of flight, light detection and ranging (TOF-LIDAR) sensor for detecting posture, motion or activity of a subject. The system comprises a novel processing module adapted to convert data obtained from a first perspective view into a second perspective view, such as a top elevation view, for the subsequent artificial intelligent (AI) analytics. In contrast to the prior art technology which requires positioning of the sensor or camera above the subject being monitored, such as at the ceiling of a room to avoid interference or occlusion by other objects or visitors in the room, the system of the present invention can be provided or arranged basically at any locations or positions in the room, such as being mounted at a place horizontal to the subject, on a bench-top, or at a corner of the room. The system is therefore highly versatile and is convenient especially for use in healthcare settings such as in hospitals, nursing homes or elderly facilities in which bed arrangement may often change depending on usage and level of occupancy of the room. Multiple sensors may further be provided to monitor a space in a synchronized manner to improve sensitivity and thus accuracy of the detection. Furthermore, the system of the present invention negates the use of any image or video-capturing devices, and that all data obtained, processed and stored are in the form of digital signals. No images or videos will therefore be kept by the system to thereby protect privacy of the subjects being monitored. The use of depth image for data processing and the analytical steps allows further benefits in preserving privacy of the subjects, as the representation by gradient or variation in luminance of the depth image enables personal identifications, body features, facial and clothing features, and/or other distinguishable features or details of the subjects to be substantially masked or concealed to protect privacy. The system of the present invention is therefore compact, versatile and is highly sensitive and accurate in detecting potential risks of the subject being monitored.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims hereof, any element expressed as a means for performing a specified function is intended to encompass any way of performing that function including, for example, a) a combination of circuit elements that performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. It is thus regarded that any means that can provide those functionalities are equivalent to those shown herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

I claim:

1. A method of monitoring a subject, comprising the steps of:
   monitoring, via a sensor, from a first angle of detection, a space in which the subject is located to obtain data of the subject from a first perspective view in accordance with the first angle of detection; wherein the monitoring step comprises emitting, via an emitter, electromagnetic radiation at the first angle of detection towards the subject, and receiving, via a receiver, electromagnetic radiation reflected from the subject thereby determining distance information of the subject relative to the sensor; and processing, via the sensor, the distance information of the subject into the data of the subject;
   converting, via a processing module, the obtained data of the subject into a three-dimensional data set; and processing, via the processing module, the three-dimensional data set to create an image of the subject from a second perspective view, said second perspective view being created at a second angle different from the first angle of detection;

analyzing, via an analyzing module, the created image from the second perspective view to determine, calculate, or select one or more characteristics relating to activity of the subject being monitored.

2. The method according to claim 1, wherein the monitoring step comprises a time of flight (TOF) measurement.

3. The method according to claim 1, wherein the three-dimensional data set comprises a three-dimensional point cloud data (PCD); wherein the converting step comprises processing the data of the subject from the first perspective view into a point cloud data from the first perspective view.

4. The method according to claim 3, wherein the converting step further comprises converting the point cloud data from the first perspective view into a point cloud data from the second perspective view.

5. The method according to claim 4, wherein the processing step further comprises processing the point cloud data from the second perspective view into a depth image from the second perspective view.

6. The method according to claim 1, wherein the first perspective view is different to the second perspective view; wherein the second perspective view is a top elevation view of the subject being monitored.

7. The method according to claim 1, wherein the one or more characteristics relating to activity of the subject being monitored comprises one or more of a posture, a motion, an orientation and a speed of motion of the subject being monitored.

8. The method according to claim 7, wherein the activity comprises one or more of lying down, sitting, standing, walking, falling, exiting bed, and exiting the space being monitored.

9. The method according to claim 1, wherein the analyzing step comprises processing based on a machine learning algorithm of a computer implemented algorithm.

10. The method according to claim 1, further comprising generating one or more alert signals in response to the activity of the subject being monitored.

11. A system for use in monitoring a subject, comprising:
a sensor adapted to monitor, from a first angle of detection, a space in which the subject is located to obtain data of the subject from a first perspective view in accordance with the first angle of detection; wherein the sensor comprises an emitter adapted to emit electromagnetic radiation at the first angle of detection towards the subject, and a receiver adapted to receive electromagnetic radiation reflected from the subject thereby determining distance information of the subject relative to the sensor; wherein the sensor is adapted to process the distance information of the subject into the data of the subject;
a processing module adapted to convert the obtained data of the subject into a three-dimensional data set, and process the three-dimensional data set to create an image of the subject from a second perspective view, said second perspective view being created at a second angle different from the first angle of detection; and
an analyzing module adapted to analyze the created image from the second perspective view to determine, calculate, or select one or more characteristics relating to activity of the subject being monitored.

12. The system according to claim 11, wherein the sensor comprises a time of flight (TOF) sensor.

13. The system according to claim 11, wherein the sensor comprises a light detection and ranging (LIDAR) sensor.

14. The system according to claim 11, wherein the data of the subject comprises a depth image from the first perspective view.

15. The system according to claim 11, wherein the three-dimensional data set comprises three-dimensional point cloud data (PCD).

16. The system according to claim 11, wherein the second perspective view is a top elevation view of the subject being monitored.

17. The system according to claim 11, wherein the analyzing module comprises a machine learning module adapted to conduct artificial intelligence analytic.

18. The system according to claim 11, further comprising a signaling module for generating one or more alert signals in response to the activity of the subject being monitored.

* * * * *